United States Patent
Williams

[19]

[11] Patent Number: 6,036,488
[45] Date of Patent: Mar. 14, 2000

[54] PIVOTAL MOUNTING BOSS FOR MANDIBULAR AND MAXILLARY ARCH EXPANDER AND JAW REPOSITIONER

[76] Inventor: Michael O. Williams, 58 Shoreline La., Gulfport, Miss. 30053

[21] Appl. No.: 09/143,071

[22] Filed: Aug. 28, 1998

Related U.S. Application Data

[63] Continuation-in-part of application No. 09/065,344, Apr. 23, 1998, Pat. No. 5,919,042.

[51] Int. Cl.[7] .................................................... A61C 3/00
[52] U.S. Cl. .................................. 433/19; 433/7; 433/17
[58] Field of Search .................................. 433/19 OR, 5, 433/7, 17, 23, 18

[56] References Cited

U.S. PATENT DOCUMENTS

| | | | |
|---|---|---|---|
| 1,137,298 | 4/1915 | Walker | 433/18 |
| 1,142,467 | 6/1915 | Walker | 433/21 |
| 1,217,374 | 2/1917 | Walker | 433/11 |
| 2,334,894 | 11/1943 | Atkinson | 433/5 |
| 3,043,005 | 7/1962 | Morris | 433/179 |
| 3,525,153 | 8/1970 | Gerber | 433/21 |
| 3,762,050 | 10/1973 | Dal Pont | 433/21 |
| 4,144,643 | 3/1979 | Krygier | 433/7 |
| 4,192,069 | 3/1980 | McAndrew | 433/21 |
| 4,245,986 | 1/1981 | Andrews | 433/5 |
| 4,347,054 | 8/1982 | Kraus et al. | 433/7 |
| 4,354,834 | 10/1982 | Wilson | 433/21 |
| 4,373,913 | 2/1983 | McAndrew | 433/7 |
| 4,375,355 | 3/1983 | Dahan | 433/5 |
| 4,375,962 | 3/1983 | DeWoskin | 433/5 |
| 4,382,783 | 5/1983 | Rosenberg | 433/19 |
| 4,384,851 | 5/1983 | McAndrews | 433/7 |
| 4,433,956 | 2/1984 | Witzig | 433/7 |
| 4,439,149 | 3/1984 | Devincenzo | 433/6 |
| 4,462,800 | 7/1984 | Jones | 433/22 |
| 4,472,139 | 9/1984 | Rosenberg | 433/19 |
| 4,509,918 | 4/1985 | Clark | 433/5 |
| 4,619,609 | 10/1986 | Clark | 433/6 |
| 4,671,767 | 6/1987 | Biechman et al. | 433/19 |
| 4,723,910 | 2/1988 | Keller | 433/7 |
| 4,795,342 | 1/1989 | Jones | 433/22 |
| 4,871,310 | 10/1989 | Vardimon | 433/19 |
| 5,064,370 | 11/1991 | Jones | 433/21 |
| 5,242,304 | 9/1993 | Truax et al. | 433/177 |
| 5,266,028 | 11/1993 | Adkisson | 433/18 |
| 5,324,196 | 6/1994 | Magill | 433/19 |
| 5,439,377 | 8/1995 | Milanovich | 433/7 |
| 5,443,384 | 8/1995 | Franseen et al. | 433/18 |
| 5,505,616 | 4/1996 | Harwell | 433/21 |
| 5,645,422 | 7/1997 | Williams | 433/7 |

OTHER PUBLICATIONS

Introducing the RMO Clark Trombone and Lingual Arch Developer.

Maxillary Expander Using Light, Continuous Dorce and Autoblocking, M. Ali Darendeliler, DDS,MSD and Carlo Lorenzon, DMD—JCO/Apr. 1996.

*Primary Examiner*—John J. Wilson
*Attorney, Agent, or Firm*—Paul M. Denk

[57] ABSTRACT

An improved pivotal mounting boss for attachment to front or rear orthodontic bands on a mandibular arch expander and a maxillary arch expander. The pivotal mounting boss includes a base casing that is soldered or welded to the orthodontic band. A screw is threadedly engaged in the base casing. The base casing has an opening formed therein for the insertion of an arch wire. The opening can be preangulated to assist in root angulation when the arch wire is inserted.

10 Claims, 4 Drawing Sheets

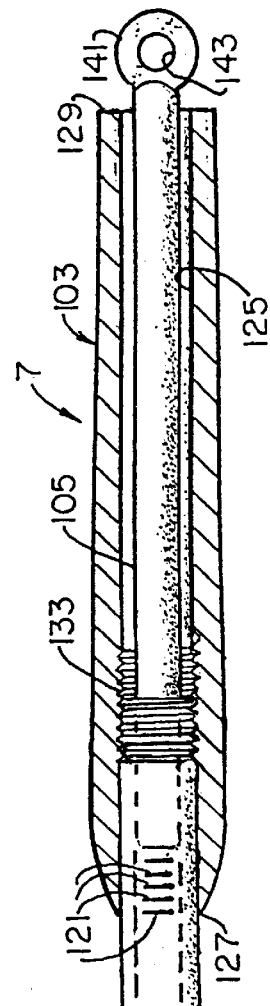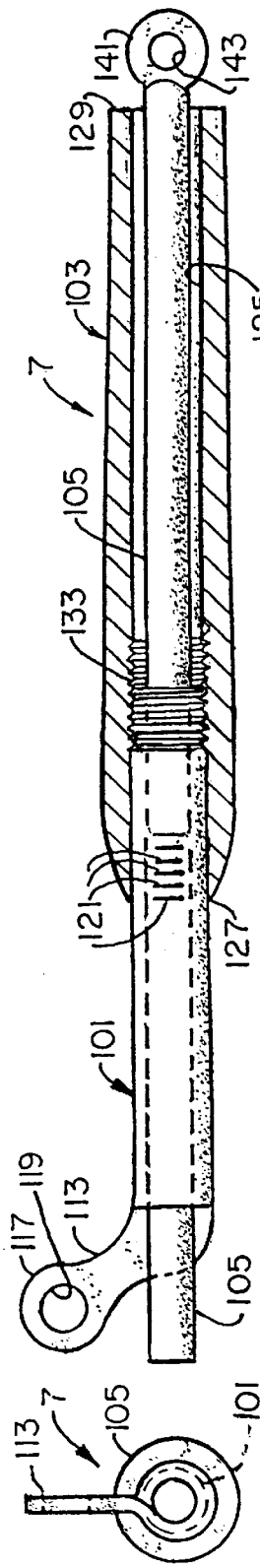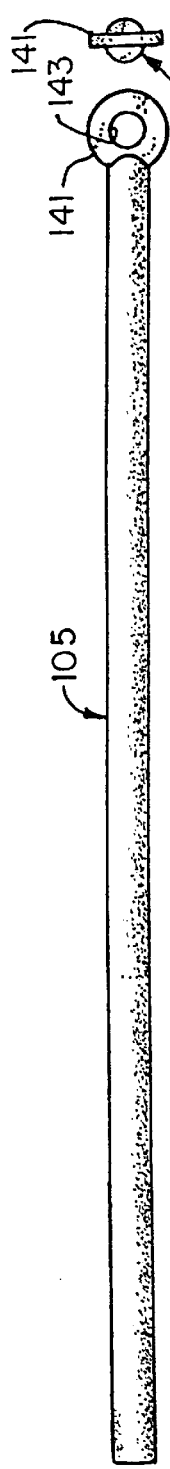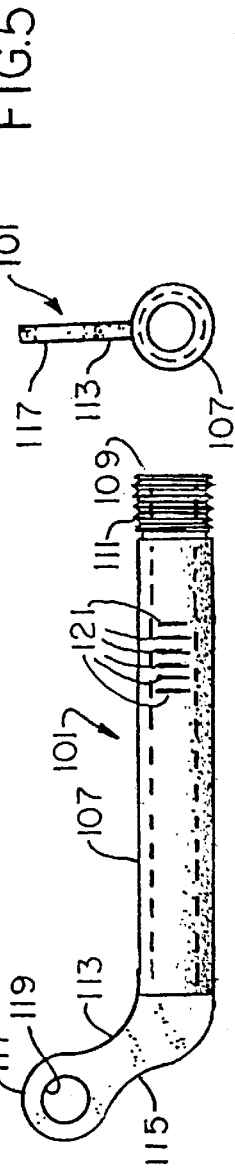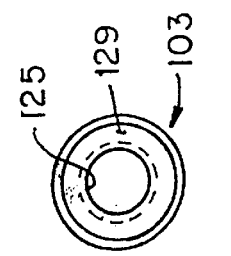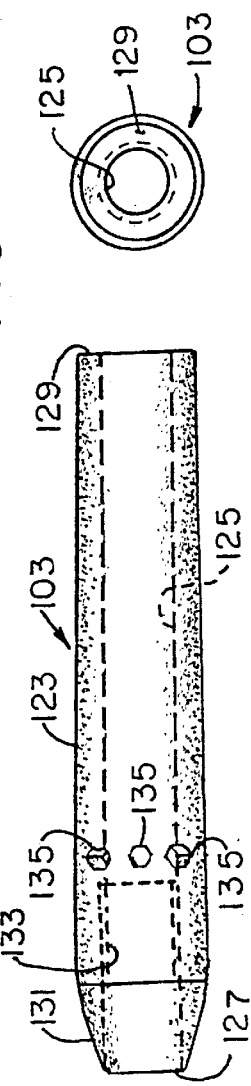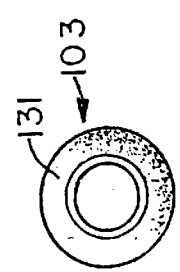

PIVOTAL MOUNTING BOSS FOR MANDIBULAR AND MAXILLARY ARCH EXPANDER AND JAW REPOSITIONER

CROSS-REFERENCE TO RELATED APPLICATIONS

This application is a continuation-in-part of application Ser. No. 09/065,344, filed Apr. 23, 1998, now U.S. Pat. No. 5,919,042, which is related to the inventions shown and described in U.S. Pat. No. 5,645,422 and application Ser. No. 08/688,110, filed Jul. 29, 1996, both of which are incorporated herein by reference.

STATEMENT REGARDING FEDERALLY SPONSORED RESEARCH OR DEVELOPMENT

Not Applicable.

BACKGROUND OF THE INVENTION

This invention relates generally to orthodontic devices and, in particular, to an improved pivot casing for a fixed mandibular arch and maxillary arch expanders which are connected together to allow for forward posturing of the mandible on closure.

Orthodontists treating children often need to gain space in a child's mouth for unerupted mandibular incisors and to increase intercanine distance for narrow archforms, as well as to distilize mandibular first molars so that a total increase of archlength is available in the lower dental arch from first molar to first molar. Furthermore, the orthodontist may want to expand the palate correspondingly.

Mandibular and maxillary arch expanders are known in the art to expand and lengthen the mandibular and maxillary archlengths. The use of such arch expanders help avoid the need for tooth extraction of permanent teeth due to overcrowding. However, such mandibular arch expanders are rather bulky in design, impede tongue mobility, are uncomfortable to wear, and interfere with good oral hygiene. The devices must be substantial in design to resist torquing or leverage mechanics during chewing.

To facilitate corresponding enlargement of the maxillary and mandibular arches, telescoping mechanisms have been employed which encourage forward repositioning of the lower jaw as the patient closes into occlusion. Such devices are commonly referred to as Herbst appliances. Current Herbst appliances include a hollow tube and a rod which is telescopically received in the tube. The tube is connected to the maxillary arch expander and the rod is connected to the mandibular arch expander. Generally, the tube and rod are connected to a band or stainless steel crown by a pivoting connection. The pivot generally comprises a base casing which is soldered or welded to the band or crown and a screw that is inserted through an eye formed on the end of the hollow tube or rod. The screw threadedly engages the base casing and tightened, leaving enough clearance for the eye to pivot about the screw. Often the orthodontist uses an arch wire connected between the two ends of the arch expander. In the past, to accommodate the arch wire, the orthodontist or technician first must attach a rectangular wire tube to the band or crown and then attach the base case on top of the rectangular tube. This arrangement has a relatively high profile caused by the stacking of the rectangular tube and base casing along with the increased solder mass.

BRIEF SUMMARY OF THE INVENTION

It is a primary object of the present invention to provide an improved pivotal mounting boss that can accommodate an arch wire for a mandibular expander.

Another object is to provide such an improved pivotal mounting boss that is integral and does not require the use of a separate arch wire tube.

Still another object of the invention is to provide a pivotal mounting boss that allows for low profile soldering or welding.

Yet another object of the invention is to provide pivotal mounting boss that can accommodate an arch wire for a mandibular expander that is more comfortable for the patient.

Another object of the invention is to provide pivotal mounting boss that can accommodate an arch wire for a mandibular expander that can have a pretorqued and preangulated arch wire opening in the base casing that assists in root angulation when the arch wire is inserted.

Another object of the invention is to provide pivotal mounting boss that can accommodate an arch wire for a mandibular expander that is easy to manufacture, efficient to install, and well suited for its intended purposes.

These and other objects will become apparent to those skilled in the art upon a review of the following disclosure and accompanying drawings.

Briefly stated, the improved pivotal mounting boss for attachment to front or rear orthodontic bands on a mandibular arch expander and a maxillary arch expander. The pivotal mounting boss includes a base casing that is soldered or welded to the orthodontic band. A screw is threadedly engaged in the base casing. The base casing has an opening formed therein for the insertion of an arch wire. The opening can be preangulated to assist in root angulation when the arch wire is inserted.

The orthodontic bands are interconnected by a pair of adjustable connector assemblies. The connector assemblies include an expandable tube assembly and a rod which extends through the expandable tube assembly such that the tube and the rod are telescopically movable relative to each other. The expandable tube assembly has an eye at a first end thereof for the insertion of the pivotal mounting boss screw to pivotally secure the connector to the rear orthodontic band of the maxillary arch. The rod has an eye adjacent a second end of the expandable tube assembly for the insertion of the pivotal mounting boss screw to be connected to base casing attached to the front orthodontic bands of the mandibular arch expander.

BRIEF DESCRIPTION OF THE SEVERAL VIEWS OF THE DRAWINGS

FIG. 2 is a side elevational view of the telescoping assembly, partially in cross-section;

FIG. 3 is a front plan view of the telescoping assembly;

FIG. 4 is a side elevational view of a rod of the telescoping assembly;

FIG. 5 is a front elevational view of the rod;

FIG. 6 is a side elevational view of a posterior tube of the telescoping assembly;

FIG. 7 is a rear elevational view of the posterior tube;

FIG. 8 is a side elevational view of an anterior tube of the telescoping assembly;

FIG. 9 is a front end elevational view of the anterior tube;

FIG. 10 is a back end elevational view of the anterior tube;

Corresponding reference numerals will be used throughout the several figures of the drawings.

DETAILED DESCRIPTION OF THE INVENTION

The following detailed description illustrates the invention by way of example and not by way of limitation. This description will clearly enable one skilled in the art to make and use the invention, and describes adaptations, and variations of the invention, including what I presently believe is the best mode of carrying out the invention.

Figure 1:
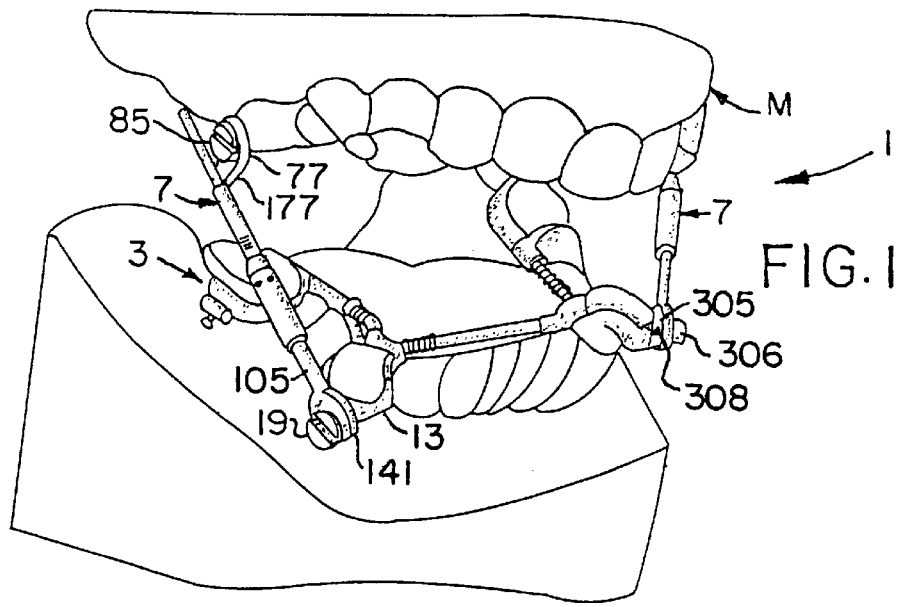
FIG. 1 is a perspective view of a mandibular arch expander and maxillary arch expander which are shown mounted in a mold and connected by a telescoping assembly of the present invention.
Figure 1A:
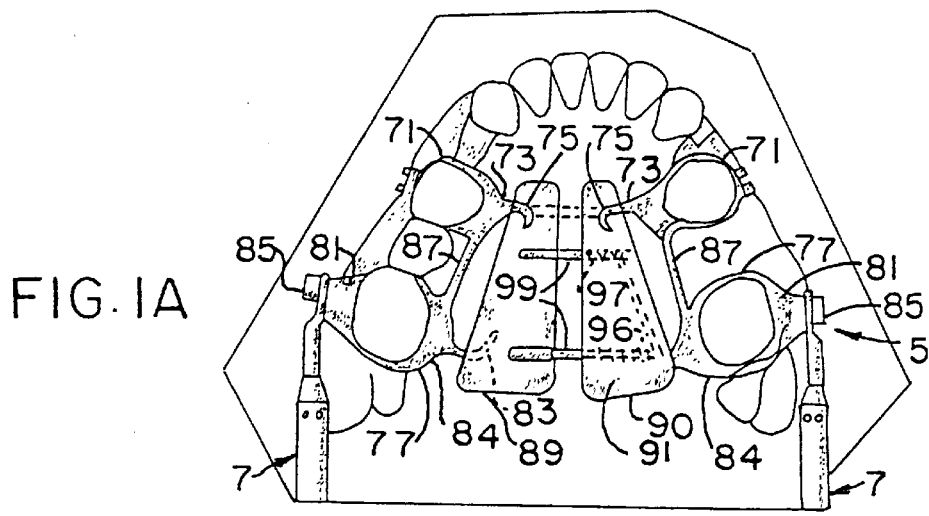
FIG. 1A is a bottom plan view of the maxillary arch expander mounted in the mold with the telescoping assembly mounted thereto.
Figure 1C:
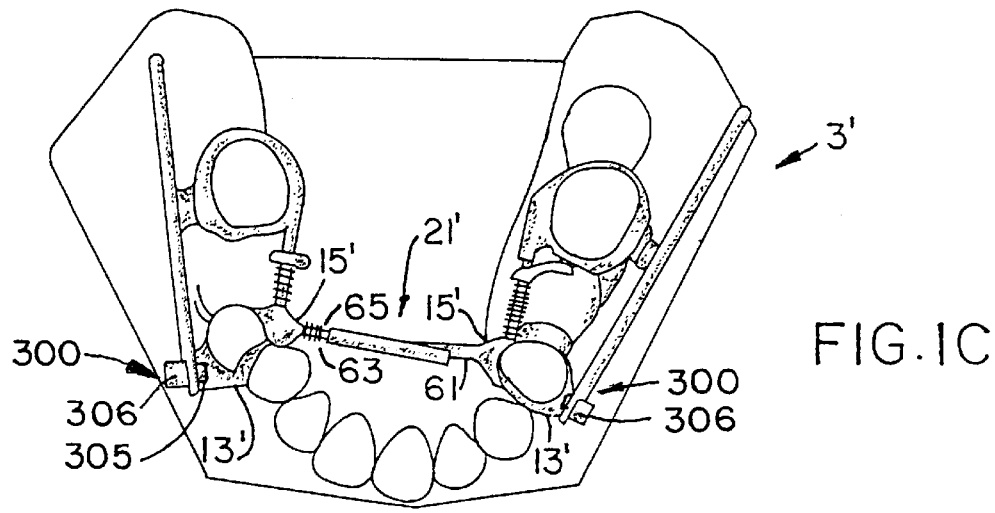
FIG. 1C is a top plan view similar to that of FIG. 1B, but with an alternative mandibular arch expander.
Figure 1B:
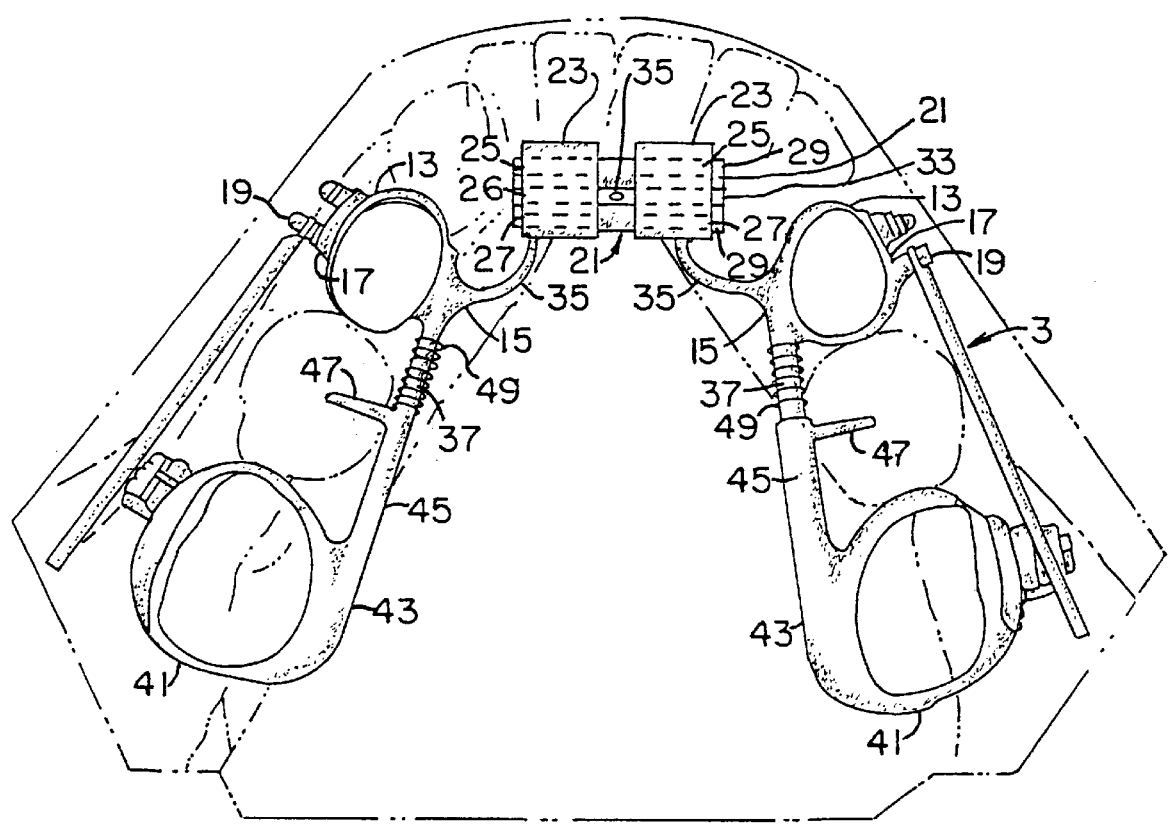
FIG. 1B is a top plan view of the mandibular arch expander mounted in the mold with the telescoping assembly mounted thereto.

Turning initially to FIGS 1–1B, an orthodontic appliance 1 of the present invention is shown mounted in a mold M of a mouth. Although the appliance 1 is shown mounted in a mold, it will be appreciated that it is designed for use in a human mouth to increase the size of a child's mouth so that the child's permanent teeth will not be crowded when they erupt. This will reduce the need for extractions of permanent teeth. The appliance 1 includes a mandibular arch expander 3, a maxillary arch expander 5, and a pair of telescoping assemblies 7 which extend between and connect the mandibular and maxillary arch expanders 3 and 5, as described below.

The mandibular and maxillary arch expanders 3 and 5 are substantially the same as the arch expanders set forth in my above noted U.S. Pat. No. 5,645,422, which is incorporated herein by reference. The mandibular arch expander 3 (FIG. 1B) has a pair of spaced apart forward orthodontic bands 13 which are adapted to attach to the mandibular first primary molars. Bands 13 each have a boss 15 positioned on the lingual side of the bands and a boss 17 positioned on the buccal side of the bands. The buccal bosses 17 are adapted to receive screws 19 to connect the telescoping assemblies 7 to the mandibular arch expander 3, as will be discussed below. The respective bosses 15 and 17 are integrally formed on the respective bands to provide a substantial metallic body for the attachment of other elements to be described hereinafter. The improved pivotal mounting boss which can accommodate an arch wire, which is the subject matter of this invention, will be described in greater detail below.

The bands 13 are interconnected by an expansion complex 21. The expansion complex 21 has a pair of metal blocks 23. The blocks 23 each have three bores 25, 26, and 27 formed laterally therethrough. The bores 25, 26, and 27 of the two blocks 23 are in substantial horizontal alignment. Aligning pins 29 extend through the outer bores 25 and 27. The respective aligning pins 29 are slightly undersized relative to the respective bores 25 and 27 so that the blocks 23 will slide relative to the pins 29. The middle bores 26 are threaded and receive a threaded screw 33. There is at least one hole 35 formed through the middle of screw 33 between the oppositely threaded ends. The hole 35 accommodates the insertion of a small tool to turn screw 33. It will be appreciated that threaded screw 33 has oppositely threaded ends. Therefore, when screw 33 is rotated in one direction, the blocks 23 are moved away from each other and when screw 33 is rotated in the opposite direction, the blocks 23 are drawn toward each other. The blocks 23 slide on the aligning pins 29 and the aligning pins serve to stabilize the expansion screw complex.

The blocks 23 are mounted to the lingual bosses 15 by curved arms 35 which extend between the bosses 15 and the block 23. The curved arms 35 can be of any appropriate length and curvature to suitably engage the patient's teeth. The mold M is made following conventional procedures and the arms 35 are fabricated to be the appropriate length and curvature. The arms 35 then are soldered to the appropriate boss 15 and to the expansion screw complex 21.

A rod 37 extends rearwardly from each of the lingual bosses 15. The rod 37 can be a small hollow tube, to reduce weight, or can be a solid rod. A stated above, the exact position on the respective bosses 15 where the rods 37 are attached and the angle at which the rod 37 extends from the bosses 15 depends upon the patient and the patient's needs. It will be appreciated that arms 35 and rods 37 can be one integral piece appropriately bent to form the arm and the rod or the arm and rod can be separate pieces.

The mandibular arch expander 3 also has a pair of spaced apart rear orthodontic bands 41. The bands 41 generally are molar bands and, in use, are attached to the permanent first molars. Each band 41 has an integral boss 43 positioned on the lingual side of the bands. A hollow tube 45 extends forwardly from each boss 43. The hollow tubes 45 have an internal bore sized to accommodate the sliding insertion of the rods 37, as will be explained in detail below.

A pair of short wires 47 extend perpendicularly from the tubes 45. The respective short wires 45 extend buccally and serve as occlusal rests and are soldered on the respective tubes at a position corresponding to the lingual occlusal groove of the deciduous second molars bilaterally to provide extra support and stability to the tubes.

The forward pair of orthodontic bands 13 are connected to the rear pair of orthodontic bands 41 to promote molar distalization and added archlength development by a pair of spring-loaded rod and tube assemblies. Rods 37 are slidingly engaged in tubes 45. Coil springs 49 are positioned around rod 37 and fixed between bosses 15 and the end of the tube 45. The coil springs 49 are sized so they abut the ends of the tubes 45 and do not slide over the tubes 45. The respective coil springs 49, therefore, urge the forward bands 13 away from the rear bands 41 to increase palate length.

The coil springs 49 have a preset tension. The preset tension of the spring is selected by the orthodontist to effect the appropriate mesial distal archlength development in the bicuspid area.

An alternative embodiment of the mandibular arch expander 3' of the present invention is shown in FIG. 1C.

The mandibular arch expander 3' is substantially identical to the mandibular arch expander 3 shown in FIG. 1B. It varies, however, in the construction of the expansion complex 21'. The arch expander 3' includes spaced apart forward orthodontic bands 13' having lingual bosses 15'. The expansion complex 21' includes a hollow tube 61 extending from one boss 15' and a rod 63 extending from the other boss 15'. The angles at which the tube 61 and rod 63 extend from the respective bosses depends upon the shape of the patient's mouth. The rod 63 is slidingly engaged in the tube 61. A coil spring 65 is journaled around the rod 63 and fixed between the boss 15' and the end of the tube 61. The spring 65 is sized to engage the end of the tube 61 and not slip over the tube 61. Therefore, the spring 65 urges the forward bands 13' away from each other. The spring 65 has a predetermined force to be delivered between the molars to widen the anterior canine width.

The maxillary palatal expander 5 (FIG. 1A) has a pair of spaced apart forward orthodontic bands 71 which are adapted to attach to the maxillary molars. The each band 71 has a boss 73 positioned on the lingual side of the bands. The respective bosses are integrally formed on the respective bands. There is an integral curved member or hook 75 extending inwardly or lingually from the bosses 73.

A pair of spaced apart rear orthodontic bands 77 are positioned rearwardly of the forward bands 71. The bands 77 each have an integral lingual boss 84 and an integral buccal boss 81. The lingual bosses 84 have an integral curved member or hook 83. The buccal bosses 81 each have a screw hole to revive a screw 85 to connect the telescoping tube assemblies 7 to the maxillary arch expander 5.

The forward orthodontic bands 71 are connected to the rear orthodontic bands 77 by a rod 87. Furthermore, the hooks 75 and 83 are embedded in plastic plates 89 and 90. The respective plastic plates are molded to fit the patient's palate. Each plate, with the associated forward and rearward bands, comprises half of the expander 5. The halves of the expander 5 are biased away from each other to widen the maxillary arch. There is a substantially U-shaped rod 91 imbedded in plate 90. The rod 91 has legs which extend out from, and at substantially right angles to, the plastic plate 90. Coil springs 96 and 97 are journaled around legs, respectively. A pair of short tubes 99 are embedded in the plate 89. The tubes 99 extend out of the palate plate 89 at substantially right angles to the palate plate. The tubes 99 are on complementary alignment with the legs of the U-shaped rod 91 and are slightly oversized so that the legs can slide into the tubes. The springs 96 and 97 abut the ends of the tubes 99 and exert tension force to urge the halves of the appliance apart. The appropriate tension can be exerted by selecting springs with the appropriate tension.

To facilitate transverse development of the lower jaw relative to the upper jaw, the maxillary and mandibular arch expanders are interconnected by the telescoping Herbst-type assemblies 7, which are shown in detail in FIGS. 2–10. The two assemblies are identical and include a posterior tube 101, an anterior tube 103, and a rod 105 which extends through the two tubes 101 and 103. The posterior tube 101 includes a hollow body 107 which is open at both its front and back ends. The body 107 has an outer diameter which is substantially constant between its front and back ends. The back end 109 is externally threaded, as at 111. An arm 113 extends upwardly from the tube's body 107 at the front 115 of the body. The arm 113 has an eyelet 117 at its free end, the eyelet having a hole 119 therein. Intermediate its front and back ends, the posterior tube 101 includes a plurality of tick marks 121 which are used to indicate the amount of advancement of the anterior tube 103 over the posterior tube 101, as will be described below. The tick marks 121 are preferably separated by about one-millimeter.

The anterior tube 103 includes a hollow body 123 defining a bore 125 therethrough. The tube 103 is open at both its back and front ends 127 and 129, respectively. The front end 127 of the tube tapers inwardly, as at 131 such that the very front of the tube 103 has a smaller outer diameter than the rest of the tube's body 123. As seen in FIGS. 8 and 10, the body 123 also tapers slightly from the back of the surface 131 to the back 129 of the body 123. The tube 123 is internally threaded at its front end, as at 133. The diameter of the bore 125 is slightly greater than the outer diameter of the anterior tube 101, and the threads 111 and 133 of the tubes 101 and 103, respectively, are machined or otherwise formed so that they will mate. Thus, the anterior and posterior tubes 101 and 103 are threadedly connected together. Notches or holes 135 are formed on the exterior of the posterior tube body 123. The notches 135 are adapted to receive a tool having a correspondingly shaped head. The tool can be used to rotate the posterior tube 103 relative to the anterior tube 101 when the appliance 1 is mounted in a patient's mouth.

The rod 105 is a generally straight rod. It has a generally constant diameter slightly less than the inner diameter of the anterior tube 101, so that it may slide relative to the tube 101. At its back end, the rod 105 has an eyelet 141 having a hole 143.

Figure 1D:
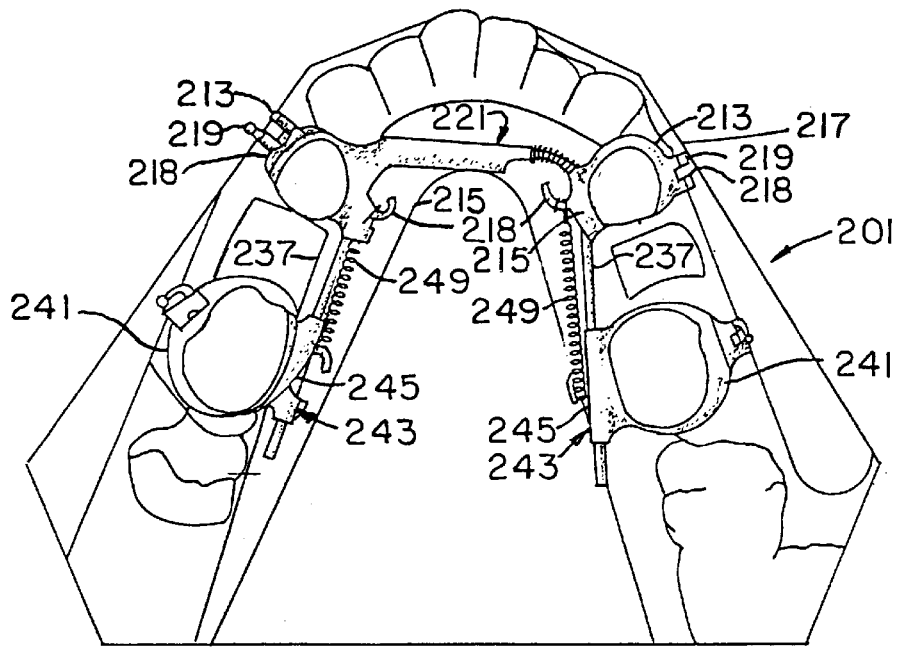
FIG. 1D is a top plan view of a mandibular molar space closer which can be used with the telescoping assembly of the present invention.

A mandibular molar space closer 201 is shown in FIG. 1D. As can be seen, it is similar to the mandibular arch expander of FIG. 1 C. The molar space closer 201 has a pair of spaced apart forward orthodontic bands 213 which are adapted to attach to the mandibular first primary molars. The bands 213 each have a boss 215 positioned on the lingual side of the bands and a boss 217 positioned on the buccal side of the bands. The buccal bosses 217 are adapted to receive screws 219 to connect the telescoping assemblies 7 to the mandibular arch expander 3. The respective bosses 215 and 217 are integrally formed on the respective bands to provide a substantial metallic body for the attachment of other elements to be described hereinafter. A hook 218 extends from the lingual boss 215 and points forwardly, toward the front of the patients mouth.

The bands 213 are interconnected by an expansion complex 221. The expansion complex 221 is identical to the expansion complex 21' of the mandibular arch expander 3'.

A rod 237 extends rearwardly from each of the lingual bosses 215. The rod 237 can be a small hollow tube, to reduce weight, or can be a solid rod. A stated above, the exact position on the respective bosses 215 where the rods 237 are attached and the angle at which the rod 237 extends from the bosses 215 depends upon the patient and the patient's needs.

The mandibular molar space closer 201 also has a pair of spaced apart rear orthodontic bands 241. The bands 241 generally are molar bands and, in use, are attached to the permanent first molars. Each band 241 has an integral boss 243 positioned on the lingual side of the bands. A hollow tube 245 extends along the lingual side of the band and through the boss 243. The hollow tubes 245 have an internal bore sized to accommodate the sliding insertion of the rods 237. The rods 237 are sized such that they will pass through the tubes 245 to extend beyond the rear of the tubes 245.

The forward pair of orthodontic bands 213 are connected to the rear pair of orthodontic bands 241 to reduce the spacing between molars using a pair of spring-loaded rod and tube assemblies. Rods 237 are slidingly engaged in tubes 245, as noted. Coil springs 249 are connected to the rod 237 behind the rear molar band 241 and to the hooks 218. As seen, in this position, the springs 249 are in an expanded state. The respective coil springs 249, therefore, pull the bands 213 and 241 towards each other to decrease the spacing between molars. The coil springs 249 have a preset tension. The preset tension of the spring is selected by the orthodontist to effect the appropriate mesial distal archlength development in the bicuspid area.

The telescoping tube assemblies 7 are assembled by threadedly connecting the anterior and posterior tubes 101 and 103, and sliding the rod 105 into the tube assembly. The rod 105 is slid into the tube assembly such that its eyelet 141 will be at the opposite end of the assembly from the anterior tube eyelet 117.

As best seen in FIG. 1, the tube assemblies 7 extend between the forward bands 13 on the mandibular arch expander 3 and the rear bands 77 on the maxillary arch expander 5. The screws 85 of the maxillary arch expander pass through the eyelet's 117 of the anterior tubes 101 to pivotally connect the tube assembly to the maxillary arch expander. Similarly, the screws 19 of the mandibular arch expander 3 pass through the eyelets 141 of the rod 105 to connect the assembly 7 to the mandibular arch expander 3.

When initially inserted in a patient's mouth, the telescoping tube assemblies 7 are sized such that the back end 129 of the posterior tube 103 is in contact with the eyelet 141 of the rod 105 when the patient's mouth is shut. This will apply a forwardly directed pressure on the mandible. Thus, with all three components (i.e., the mandibular and maxillary arch expanders 3 and 5, and the telescoping tube assemblies 7 and 8) installed in a patient's mount, the appliance 1 will allow for transverse development, archlength development, palatal expansion and mandibular advancement, simultaneously without requiring patient compliance.

By rotating the tube 103 in one direction, the tube 103 will advance over the tube 101, to shorten the overall length of the tube assembly 7. Conversely, by rotating the tube 103 in a second direction, the tube 103 will be retracted relative to the anterior tube, to increase the overall length of the tube assembly. The extent of the movement of the tubes 101 and 103 relative to each other is measured by the tick marks 121. The interior threads 33 of the tube 103 and the tick marks 121 of the tube 101 are positioned on their respective tubes, such that when the tube 101 is threaded into the tube 103, the tick marks 121 will be exposed. By rotating the two tubes relative to each other, the number of tick marks exposed increases or decreases, depending on the direction of rotation, to indicate how far the tube assembly has been lengthened or shortened by the rotation of the tubes relative to each other. Thus, by reading the number of tick marks exposed, the practitioner can determine the amount of advancement that has occurred, as well as the overall length of the assembly 7.

Figure 11:
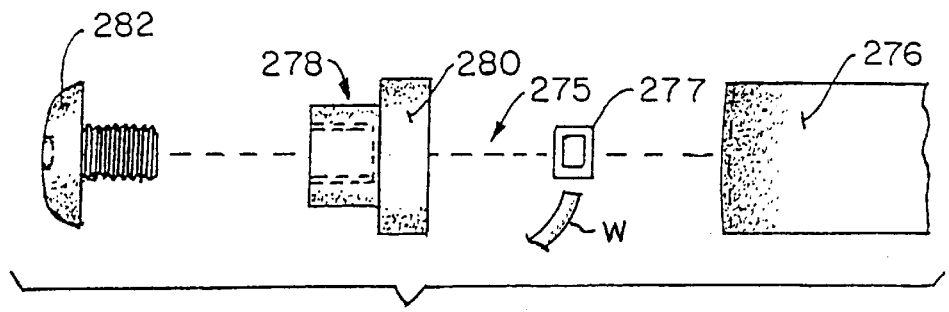
FIG. 11 is an exploded view of a prior art pivotal mounting boss assembly and an orthodontic band with a rectangular tube interposed to accommodate an arch wire.
Figure 12:
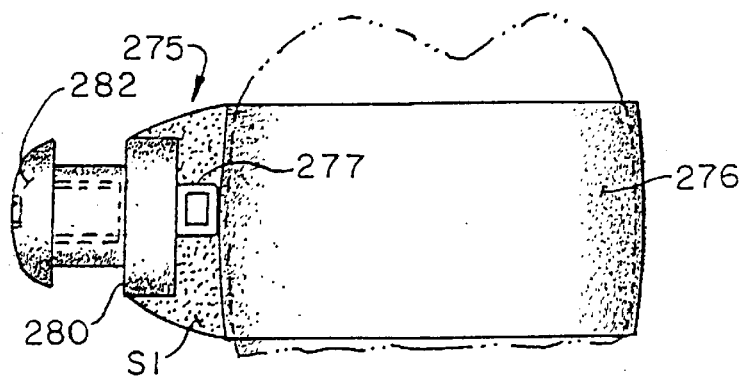
FIG. 12 is a perspective view of the prior art pivotal mounting boss assembly of FIG. 11 attached to an orthodontic band with a rectangular tube interposed to accommodate an arch wire.

A prior art mounting boss assembly gerry-rigged to accommodate an arch wire W is shown in detail in FIGS. 11 and 12 and indicated generally by reference numeral 275 shown in use with an orthodontic band 276. It will be appreciated that assembly 275 is described as attached to an orthodontic band but can be attached to a stainless steel crown as well Assembly 275 functions as the above described bosses attached to the orthodontic bands. However, assembly 275 is modified to allow the attachment of arch wires. The prior art assembly 275 includes a short segment of square tubing 277 which is attached to the band 276 by soldering S1, for example. The square tubing is position on the orthodontic band for the attachment of an arch wire W, if needed. A mounting boss 278 including a base casing 280 and a screw 282 is then soldered on top of the square tubing. It will be appreciated by those skilled in the art that the prior art assembly 275 requires a substantial solder joint S1 to secure the elements which results in a high profile boss. Moreover, installation of the boss on the band requires addition time and costs.

Figure 13:
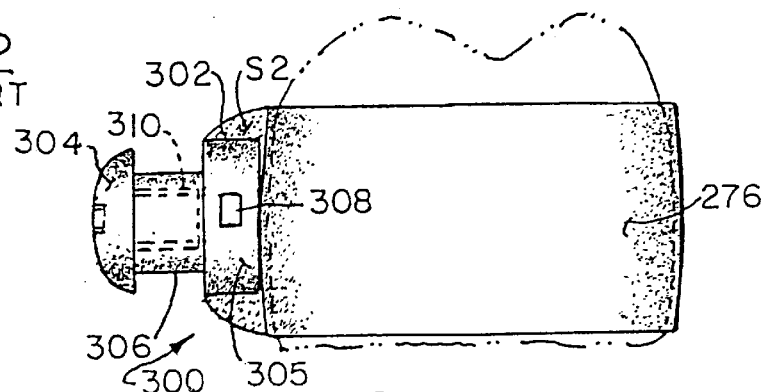
FIG. 13 is a perspective view of the improved pivotal mounting boss assembly of the present invention attached to an orthodontic band.
Figure 14:
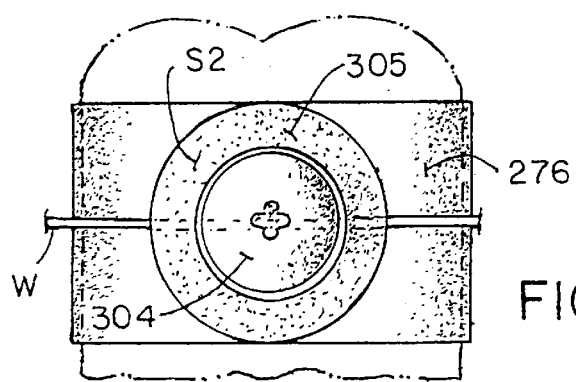
FIG. 14 is a front elevational view of the improved pivotal mounting boss assembly of the present invention attached to an orthodontic band.

An improved pivotal mounting boss is illustrated in FIG. 13 and shown in application in FIGS. 1, 1C and 2 is indicated generally by reference numeral 300. Mounting boss 300 includes a base casing 302 and a threaded screw 304. Base casing 302 includes a generally cylindrical base segment 305 and a concentric cylindrical body segment 306. Base segment 305 has an opening 308 formed therein. In the illustrated embodiment opening 308 is rectangular and is designed to accommodate a conventional arch wire W. See FIG. 14. The base segment can be position on the orthodontic band 276 and soldered in place with solder S2. It will be appreciated that the opening 308 can be positioned at a predetermined angle as desired by the orthodontist for root angulation. It will be appreciated that less solder S2 is required to attach boss 300 to the orthodontic band resulting in less bulk and a lower profile arrangement than that shown in FIG. 12.

The body segment 306 includes an internally threaded bore 310 for the threaded engagement of screw 304 The screw 304 is inserted through the eyelet of the orthodontic device described above and tightened, leaving enough clearance so that the eyelet can rotate or pivot about the screw.

In view of the above, it will be seen that the several objects and advantages of the present invention have been achieved and other advantageous results have been obtained. As various changes could be made in the above constructions without departing from the scope of the invention, it is intended that all matter contained in the above description or shown in the accompanying drawings shall be interpreted as illustrative and not in a limiting sense.

I claim:

1. A pivotal mounting boss assembly for attachment to an orthodontic band for the pivotal mounting boss of an arch expansion appliance comprising:

a base casing including a base segment for attachment to the orthodontic band, said base segment having an opening formed therein, said opening disposed to attach an arch wire, and a body segment being narrower in at least one cross sectional dimension than said base segment, and said body segment having a threaded bore formed therein; and a screw threadedly engaged in said threaded bore, said screw disposed to attach to an eyelet of an expansion appliance.

2. The pivotal mounting boss assembly of claim 1 wherein said base segment is attached to an orthodontic band by soldering.

3. In an orthodontic appliance for expanding and lengthening the mandibular and maxillary arch of a human patient, the appliance having a mandibular arch expander having a pair of forward orthodontic bands, a pair of rear orthodontic bands, a first mandibular expansion assembly to expand said mandibular arch expander, and a second mandibular expansion assembly to lengthen said mandibular arch expander the improvement comprising:

a pivotal connector assembly for attachment to an orthodontic band for the pivotal attachment of a mandibular arch expander, said pivotal connector assembly including a base casing having a base segment and a body segment extending from the base segment, said base segment being wider in cross section than said body segment, and said base segment having an opening formed therein for the insertion of an arch wire, said body segment having a threaded bore formed therein, said threaded bore terminating in the base section; and a screw threadedly engaged in said threaded bore.

4. The orthodontic appliance of claim 3 wherein said mandibular arch expander include eyelets having holes therethrough for the introduction of said screw.

5. An orthodintic appliance for expanding and lengthening the mandibular and maxillary arch of a human patient, the appliance comprising:

a mandibular arch expander having a pair of forward orthodontic bands, a pair of rear orthodontic bands;

a maxillary arch expander including a pair of forward orthodontic bands a pair of rear orthodontic bands; and a pair of adjustable connector assemblies; said connector assemblies each comprising an expandable tube assembly and a rod which extends through said expandable tube assembly; said expandable tube assembly having a mount at a first end thereof adapted to connect said tube assembly to a pivotal mounting boss assembly on said rear orthodontic band of said maxillary arch; said rod having a mount adjacent a second end of said expandable tube assembly adapted to be connected to a pivotal mounting boss assembly on said front orthodontic bands of said mandibular arch expander;

each said pivotal mounting boss assembly including a base casing for attachment to an orthodontic band, said base casing having an opening defined by at least one wall and bounded by said wall formed therein for the insertion of an arch wire, said body segment having a threaded bore formed therein and a screw insertable through said mount and threadedly engaged within said threaded bore.

6. The orthodontic appliance of claim 5 wherein the tube assembly includes a hollow posterior tube and an anterior tube which are telescopically connected.

7. The orthodontic appliance of claim 5 wherein said anterior tube includes a hollow body having an externally threaded back end and said posterior tube includes a hollow body defining a bore, said posterior tube being internally threaded at a front end of said tube; said posterior tube bore being sized to accept said anterior tube, said posterior and anterior tubes being threadedly connected together.

8. The orthodontic appliance of claim 5 wherein said posterior tube includes holes adapted to receive a tool to facilitate adjustment of the position of the posterior tube relative to the anterior tube to alter the overall length of the connection assembly.

9. The orthodontic appliance of claim 8 wherein said anterior tube includes indicators to inform a practitioner as to the length of the connection assembly.

10. A pivotal mounting boss assembly and an orthodontic band for the pivotal mounting boss of an arch expansion appliance comprising:

a base casing including a base segment for attachment to the orthodontic band, wherein said base segment is attached to said orthodontic band by soldering, said base segment having an opening formed therein, said opening disposed to attach an arch wire, and a body segment having a threaded bore formed therein; and a screw threadedly engaged in said threaded bore, said screw disposed to attach to an eyelet of an expansion appliance.

* * * * *

UNITED STATES PATENT AND TRADEMARK OFFICE
CERTIFICATE OF CORRECTION

PATENT NO. : 6,036,488

DATED : March 14, 2000

INVENTOR(S) : Michael O. Williams

It is certified that error appears in the above-identified patent and that said Letters Patent is hereby corrected as shown below:

Column 9, line 13, change "orthodintic" to --orthodontic--.

Signed and Sealed this

Twelfth Day of December, 2000

Attest:

Q. TODD DICKINSON

*Attesting Officer*   *Director of Patents and Trademarks*